United States Patent
Lin et al.

(10) Patent No.: US 9,549,993 B2
(45) Date of Patent: Jan. 24, 2017

(54) SPECIFIC DELIVERY OF TOXINS CONJUGATED WITH ANTIBODIES TO ACTIVATE MATRIPASE

(71) Applicants: RUTGERS, THE STATE UNIVERSITY OF NEW JERSEY, New Brunswick, NJ (US); GEORGETOWN UNIVERSITY, N.W., WA (US)

(72) Inventors: Siang-Yo Lin, East Brunswick, NJ (US); Joseph R. Bertino, Brantford, CT (US); Chen-Yong Lin, Falls Church, VA (US); Michael Johnson, Rockville, MD (US)

(73) Assignees: RUTGERS, THE STATE UNIVERSITY OF NEW JERSEY, New Brunswick, NJ (US); GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/433,200

(22) PCT Filed: Oct. 2, 2013

(86) PCT No.: PCT/US2013/063090
§ 371 (c)(1),
(2) Date: Apr. 2, 2015

(87) PCT Pub. No.: WO2014/055663
PCT Pub. Date: Apr. 10, 2014

(65) Prior Publication Data
US 2015/0250895 A1   Sep. 10, 2015

Related U.S. Application Data

(60) Provisional application No. 61/708,844, filed on Oct. 2, 2012.

(51) Int. Cl.
| | |
|---|---|
| A61K 47/48 | (2006.01) |
| C07K 16/40 | (2006.01) |
| A61K 31/00 | (2006.01) |
| A61K 31/704 | (2006.01) |
| A61K 31/7048 | (2006.01) |

(52) U.S. Cl.
CPC ....... *A61K 47/48646* (2013.01); *A61K 31/704* (2013.01); *A61K 31/7048* (2013.01); *A61K 47/484* (2013.01); *A61K 47/48407* (2013.01); *A61K 47/48569* (2013.01); *C07K 16/40* (2013.01); *C07K 2317/24* (2013.01); *C07K 2317/76* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 5,518,888 A * | 5/1996 | Waldman | A61K 47/48238 424/1.69 |
| 6,573,096 B1 | 6/2003 | Chen | |
| 7,355,015 B1 | 4/2008 | Dickson et al. | |
| 7,572,444 B2 | 8/2009 | Foltz et al. | |
| 8,043,620 B2 * | 10/2011 | Qian | C07K 16/18 424/142.1 |
| 8,883,429 B2 * | 11/2014 | Tomaskova | C12Q 1/701 424/130.1 |
| 2006/0171884 A1 | 8/2006 | Foltz et al. | |
| 2009/0022658 A1 | 1/2009 | Braslawsky et al. | |
| 2009/0130114 A1 | 5/2009 | Qian et al. | |
| 2009/0175873 A1 | 7/2009 | Liu | |
| 2009/0226453 A1 | 9/2009 | Herr et al. | |

FOREIGN PATENT DOCUMENTS

| | | | |
|---|---|---|---|
| WO | 96/39183 | 12/1996 | |
| WO | WO/96/39183 | * 12/1996 | ........... A61K 39/395 |
| WO | 0143773 A1 | 6/2001 | |
| WO | 2009/020645 | 2/2009 | |
| WO | 2009114335 A2 | 9/2009 | |
| WO | 2010119704 A1 | 10/2010 | |
| WO | 2010138564 A1 | 12/2010 | |
| WO | 2011063127 A1 | 5/2011 | |
| WO | 2012093340 A2 | 7/2012 | |

OTHER PUBLICATIONS

Tanimoto et al. "Transmembrane serine protease TADG-15 (ST14/Matripase/MT-SP1): expression and prognostic value in ovarian cancer", British Journal of Cancer 92: 278-283. (2005).
Lesur et al., "Covalent linkage of anthracyclines to macromoleclar carriers", Protides of teh Biological Fluids (1985), vol. 32, pp. 437-440.
International Search Report and Written Opinion dated Jan. 29, 2014, issue in Application No. PCT/US2103/063090.
International Search Report and Written Opinion dated Mar. 21, 2011, issue in Application No. PCT/US2010/057235.
Bertino, et al: "Abstract 2596: Targeted Delivery of Doxorubicin Conjugated with Anti-Malriptase Antibody to Treat Multiple Myeloma", American Association for Cancer Research, [retrieved on Sep. 30, 2016]. Retrieved from the Internet <URL:http://cancerres.aacrjournals.org/content/70/8_Supplement/2596>>Abstract.

* cited by examiner

*Primary Examiner* — Elly-Gerald Stoica
(74) *Attorney, Agent, or Firm* — Fox Rothschild LLP

(57) ABSTRACT

Disclosed are antibody drug conjugates (ADC) that include highly potent toxic agents with specific antibodies to target tumors. Also disclosed are related antibodies, polypeptides, nucleic acids, host cells, compositions, and uses.

11 Claims, 2 Drawing Sheets

SEQUENCE LISTING

```
<160> NUMBER OF SEQ ID NOS: 8

<210> SEQ ID NO 1
<211> LENGTH: 103
<212> TYPE: PRT
<213> ORGANISM: Artificial
<220> FEATURE:
<223> OTHER INFORMATION: Synthetic

<400> SEQUENCE: 1

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Glu Asn Thr Leu Leu
65                  70                  75                  80

Leu Met Lys Leu Pro Ser Leu Cys Tyr Gly Leu Leu Gly Ser Arg Asn
                85                  90                  95

Leu Ser Pro Arg Val Leu Gln
                100

<210> SEQ ID NO 2
<211> LENGTH: 143
<212> TYPE: PRT
```

<213> ORGANISM: Artificial
<220> FEATURE:
<223> OTHER INFORMATION: Synthetic

<400> SEQUENCE: 2

```
Leu Leu Leu Trp Ile Pro Gly Ser Thr Gly Asp Ile Val Leu Thr Gln
1               5                   10                  15

Ser Pro Ala Ser Leu Ala Val Ser Leu Gly Gln Arg Ala Thr Ile Ser
            20                  25                  30

Cys Arg Ala Ser Glu Ser Val Asp Asn Tyr Gly Ile Ser Phe Met Asn
        35                  40                  45

Trp Phe Gln Gln Lys Pro Gly Gln Pro Pro Lys Leu Leu Ile Tyr Ala
    50                  55                  60

Ala Ser Asn Gln Gly Ser Gly Val Pro Ala Arg Phe Ser Gly Ser Gly
65                  70                  75                  80

Ser Gly Thr Asp Phe Ser Leu Asn Ile His Pro Met Gly Glu Ala Asp
                85                  90                  95

Thr Ala Met Tyr Phe Cys Gln Gln Ser Lys Glu Val Pro Tyr Thr Phe
            100                 105                 110

Gly Gly Gly Thr Lys Leu Glu Ile Lys Arg Ala Asp Ala Ala Pro Thr
        115                 120                 125

Val Ser Ile Phe Pro Pro Ser Ser Glu Gln Leu Thr Ser Gly Gly
    130                 135                 140
```

<210> SEQ ID NO 3
<211> LENGTH: 312
<212> TYPE: DNA
<213> ORGANISM: Artificial
<220> FEATURE:
<223> OTHER INFORMATION: Synthetic

<400> SEQUENCE: 3

```
gaagtgaagc tggtggagtc tgggggaggc ttagtgcagc ctggagggtc ccggaaactc    60
tcctgtgcag cctctggatt cactttcagt agctttggaa tgcactgggt tcgtcaggct   120
ccagagaagg ggctggagtg ggtcgcatac attagtagtg gcagtagtac cctccactat   180
gcagacacag tgaagggccg attcaccatc tccagagaca atcccgagaa caccctgttc   240
ctgctaatga aactcccctc actatgctat ggactactgg ggtcaaggaa cctcagtccc   300
cgtgtcctcc ag                                                       312
```

<210> SEQ ID NO 4
<211> LENGTH: 429
<212> TYPE: DNA
<213> ORGANISM: Artificial
<220> FEATURE:
<223> OTHER INFORMATION: Synthetic

<400> SEQUENCE: 4

```
ctgctgctct ggattccagg ttccacaggt gacattgtgc tgacccaatc tccagcttct    60
ttggctgtgt ctctagggca gagggccacc atctcctgca gagccagcga aagtgttgat   120
aattatggca ttagttttat gaactggttc aacagaaaac caggacagcc acccaaactc   180
ctcatctatg ctgcatccaa ccaaggatcc ggggtccctg ccaggtttag tggcagtggg   240
tctgggacag acttcagcct caacatccat cctatggggg aggcagatac tgcaatgtat   300
ttctgtcagc aaagtaagga ggtcccgtac acgttcggag gggggaccaa gctggaaata   360
aaacgggctg atgctgcacc aactgtatcc atcttcccac catccagtga gcagttaaca   420
```

```
tctggaggt                                                          429

<210> SEQ ID NO 5
<211> LENGTH: 20
<212> TYPE: DNA
<213> ORGANISM: Artificial
<220> FEATURE:
<223> OTHER INFORMATION: Synthetic primer

<400> SEQUENCE: 5
cagtgtgagg tgaagctggt                                               20

<210> SEQ ID NO 6
<211> LENGTH: 19
<212> TYPE: DNA
<213> ORGANISM: Artificial
<220> FEATURE:
<223> OTHER INFORMATION: Synthetic primer

<400> SEQUENCE: 6
gcacctccag atgttaact                                                19

<210> SEQ ID NO 7
<211> LENGTH: 17
<212> TYPE: DNA
<213> ORGANISM: Artificial
<220> FEATURE:
<223> OTHER INFORMATION: Synthetic primer

<400> SEQUENCE: 7
ctgctgctct gggttcc                                                  17

<210> SEQ ID NO 8
<211> LENGTH: 20
<212> TYPE: DNA
<213> ORGANISM: Artificial
<220> FEATURE:
<223> OTHER INFORMATION: Synthetic primer

<400> SEQUENCE: 8
gcacctccag atgttaactg                                               20
```

SPECIFIC DELIVERY OF TOXINS CONJUGATED WITH ANTIBODIES TO ACTIVATE MATRIPASE

CROSS REFERENCE TO RELATED APPLICATION

This application claims priority of U.S. Provisional Application No. 61/708,844 filed on Oct. 2, 2012. The content of the application is incorporated herein by reference in its entirety.

FIELD OF THE INVENTION

This invention relates to the treatment of cellular proliferative (e.g., cancer) and other disorders by specific delivery of toxins conjugated with antibodies to activated matriptase.

BACKGROUND OF THE INVENTION

Cancer is the second leading cause of death in the United States, exceeded only by heart disease. It features an abnormal mass of malignant tissue resulting from excessive cell division. Cancer cells proliferate in defiance of normal restraints on cell growth, and invade and colonize territories normally reserved for other cells. Modes of cancer therapy include chemotherapy, surgery, radiation, and combinations of these treatments. Chemotherapy typically involves use of one or more compounds that inhibit cancer cell growth. While many cancer chemotherapeutic agents have been developed, there remains a need for more effective and specific therapy.

SUMMARY OF INVENTION

This invention provides an antibody drug conjugate (ADC) that is composed of a highly potent toxic antibiotic with specific antibodies to target tumors. ADC's combine the specificity of monoclonal antibodies (mAbs) with the potency of cytotoxic molecules, thereby delivering drug payload to the tumor sites by targeting an antigen e.g., matriptase, expressed on the surface of malignant cells. This invention allows selective delivery of cytotoxic agents thereby reducing the systemic toxicity associated with traditional chemotherapeutics to avoid the unwanted side effects.

Accordingly, in one aspect, the invention provides an isolated antibody, or antigen binding portion thereof, that includes (i) a first sequence that is at least 70% (e.g., 75, 80, 85, 90, 95, 99%, 100%, inclusive) identical to SEQ ID NO: 1 and (ii) a second sequence that is at least 70% (e.g., 75, 80, 85, 90, 95, 99%, or 100%, inclusive) identical to SEQ ID NO: 2, where the antibody specifically recognizes the active form of matriptase (i.e., activated matriptase). Preferably, the antibody recognizes both the free form and complex form of activated matriptase. In one embodiment, the isolated antibody, or antigen binding portion thereof, contains a heavy chain and a light chain that have the sequences of SEQ ID NOs: 1 and 2, respectively. Examples include the M69 and M17 antibodies disclosed in the examples below. The above-mentioned antibody can be a single-chain antibody, a monoclonal antibody, a humanized monoclonal antibody, or a human monoclonal antibody, or other antibody variants disclosed herein. In one example, the isolated antibody, or antigen binding portion thereof, is conjugated with a cytotoxic agent. Examples of the cytotoxic agent include doxorubicin, auristatin, maytansinoid, neocarzinostatin (NCS), or a derivative thereof.

In a second aspect, the invention provides an isolated polypeptide having a sequence that is at least 70% (e.g., 75, 80, 85, 90, 95, or 99%, inclusive) identical to SEQ ID NO: 1 or 2. In one embodiment, the polypeptide comprises, consists essentially of, or consists of SEQ ID NO: 1 or 2.

In a third aspect, the invention features an isolated nucleic acid having a sequence encoding a complementarity determining region (CDR), a heavy chain variable region, or a light chain variable region of the above-mentioned antibody, or antigen binding portion thereof, or the polypeptide. Examples of the nucleic acid include SEQ ID NOs: 3 and 4 shown below. The invention also provides a vector having the nucleic acid and a cultured cell having the nucleic acid or vector.

The aforementioned nucleic acid, vector, and host cell can be used for producing an antibody or a polypeptide of this invention. Accordingly, this invention also provides a method of producing a polypeptide or antibody. The method includes culturing the host cell in a medium under conditions permitting expression of a polypeptide or antibody encoded by the nucleic acid, and purifying the polypeptide or antibody from the cultured cell or the medium of the cell.

In a fourth aspect, the invention provides a pharmaceutical composition having (i) at least one of the above-mentioned antibody, or antigen binding portion thereof, and (ii) a pharmaceutically acceptable carrier.

In a fifth aspect, the invention provides a method of preventing or treating a cellular proliferative disorder. The method includes the steps of identifying a subject in need of such prevention or treatment, and administering to the subject a first therapeutic agent having a therapeutically effective amount of at least one of the above-mentioned antibody, or antigen binding portion thereof. One example of the cellular proliferative disorder is cancer, including, but not limited to, breast cancer, prostate cancer, colon cancer, stomach cancer, ovary cancer, pancreas cancer, liver cancer, lung cancer, mesothelioma, melanoma, glioma (e.g., glioblastoma), myeloma, and lymphoma. Preferably, a second therapeutic agent can be administered to the subject.

Finally, the invention provides an isolated polypeptide, an isolated antibody or antigen binding portion thereof, a nucleic acid, a host cell, pharmaceutical composition, or uses thereof as shown and described herein.

The details of one or more embodiments of the invention are set forth in the description below. Other features, objects, and advantages of the invention will be apparent from the description and from the claims.

DETAILED DESCRIPTION OF THE INVENTION

Figure 1:
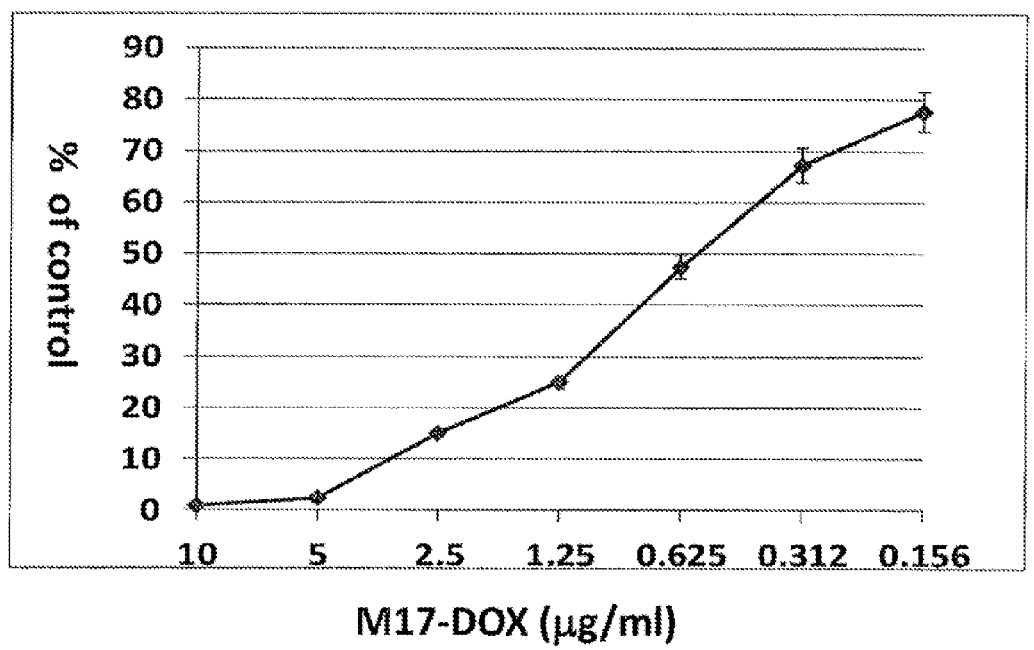
FIG. 1 is a diagram showing cytotoxic efficacy of M17-DOX toward breast cancer cells in vitro, where breast cancer cells, BDA-MB468, were treated with M17-DOX at indicated concentration for 96 h, and cell proliferation assay with colorimetric method (MTS assay; PROMEGA) was used to assess cytotoxic effects the conjugate. The survival of the cells was quantified as percentages of control group of untreated cells. Values represent the mean±s.e.m. from three experiments.
Figure 2:
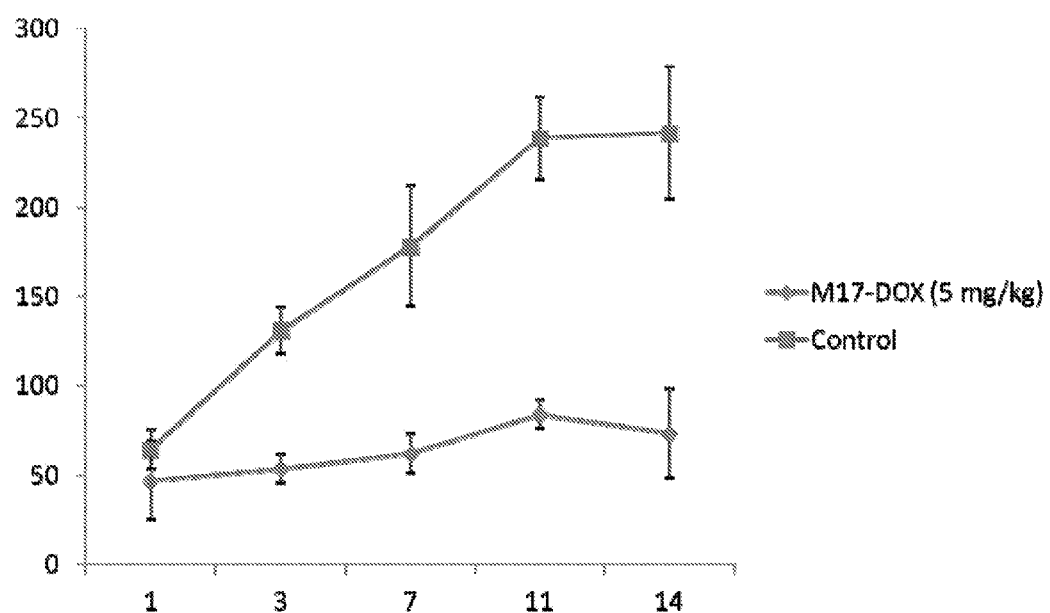
FIG. 2 is a diagram showing in vivo efficacy of M17-DOX in a breast tumor MDA-MB-468 xenograft mode over a period of 14 days. The numbers of the Y-axis represent the average tumor volumes of each group. The tumor volume was calculated using the formula: 0.5×(largest diameter) ×(smallest diameter)2.

This invention provides agents and methods for treatment of cellular proliferative disorders and other disorders by cell-specific delivery of toxic agents conjugated with antibodies to activated matriptase.

Matriptase is a type II transmembrane serine protease expressed in most human epithelia, where it is coexpressed with its cognate transmembrane inhibitor, hepatocyte growth factor activator inhibitor (HAI)-1. Activation of matriptase can be induced under hypoxic conditions, often occurring in tumors due, at least in part, to the hypoxia-driven glycolysis pathway that in turn results in acidosis. Targeting tumor hypoxia therefore can be used to improve cancer therapy, and, as disclosed herein, the findings of the sensitization of cancer cells to M69-NCS and M17-NCS suggest that ADCs targeting activated matriptase may be enhanced by hypoxic tumor environments.

One of the unique features of the M69 and M17 antibodies is their specific bindings to both free activated matriptase as well as complex form of active enzyme and its inhibitor HAI-1 or HAI-2. While a number of anti-active matriptase mAbs are known, M69 and M17 can recognize both the free and complex forms of the activated enzyme. This peculiar specific affinity is of critical importance for clinical application, since matriptase activation is immediately followed by inactivation through forming complex with its inhibitor HAI-1 or -2 on the surface of epithelial carcinoma cells as a result of excessive abundance of the inhibitors in the surroundings.

A cellular proliferative disorder refers to a disorder characterized by uncontrolled, autonomous cell growth, including malignant and non-malignant growth. Examples of cellular proliferative and/or differentiation disorders include cancer, e.g., carcinoma, sarcoma, metastatic disorders or hematopoietic neoplastic disorders, e.g., leukemia. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemia, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to multiple myeloma, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia, Hodgkin's disease and Reed-Sternberg disease.

As used herein, the percent identity of two amino acid sequences or of two nucleic acids is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

An "isolated polypeptide" refers to a polypeptide that has been separated from other proteins, lipids, and nucleic acids with which it is naturally associated. The polypeptide can constitute at least 10% (i.e., any percentage between 10% and 100% inclusive, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods.

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

The amino acid composition of the above-mentioned peptide/polypeptide/protein may vary without disrupting the ability to recognize an activated matriptase. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 or 2 is preferably replaced with another amino acid residue from the same side chain family. Alternatively, mutations can be introduced randomly along all or part of the sequences, such as by saturation mutagenesis, and the resultant mutants can be screened for the ability to bind to the activated matriptase to identify mutants that retain the activity as descried below in the examples.

A functional equivalent of a peptide, polypeptide, or protein of this invention refers to a polypeptide derivative of the peptide, polypeptide, or protein, e.g., a protein having one or more point mutations, insertions, deletions, truncations, a fusion protein, or a combination thereof. It retains substantially the above-mentioned activity of recognizing the activated from of matriptase. The isolated polypeptide can contain SEQ ID NO: 1 or/and 2 or a functional fragment thereof. In general, the functional equivalent is at least 70% (e.g., any number between 70% and 100%, inclusive, e.g., 70%, 80%, 85%, 90%, 95%, and 99%) identical to SEQ ID NO: 1 or 2.

A polypeptide described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Alternatively, the peptides/polypeptides/proteins of the invention can be chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The present invention also provides a nucleic acid that encodes any of the polypeptides mentioned above. Preferably, the nucleotide sequences are isolated and/or purified. A nucleic acid refers to a DNA molecule (for example, but not limited to, a cDNA or genomic DNA), an RNA molecule (for example, but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The present invention also provides recombinant constructs or vectors having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or viruses. In a preferred embodiment, the promoter is a tissue specific promoter that drives mRNA synthesis in a cell or tissue of interest.

The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vector containing the appropriate nucleic acid sequences as described above, as well as an appropriate promoter or control sequence, can be employed to transform an appropriate host to permit the host to express the polypeptides or antibodies described above (e.g., SEQ ID NO: 1 or 2). Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned polypeptides or antibodies by transfecting a host cell with an expression vector having a nucleotide sequence that encodes one of the polypeptides or antibodies. The host cells are then cultured under a suitable condition, which allows for the expression of the polypeptide or antibodies.

Antibodies

This invention also provides various antibodies that specifically recognize the active form of matriptase. Examples include M69 and M17 disclosed in the examples below. The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein having at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)).

The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)). The described invention provides variable region antigen-binding sequences derived from human antibodies. Accordingly, chimeric antibodies of primary interest herein include antibodies having one or more human antigen binding sequences (for example, CDRs) and containing one or more sequences derived from a non-human antibody, for example, an FR or C region sequence. In addition, chimeric antibodies included herein are those comprising a human variable region antigen binding sequence of one antibody class or subclass and another sequence, for example, FR or C region sequence, derived from another antibody class or subclass.

A "humanized antibody" generally is considered to be a human antibody that has one or more amino acid residues introduced into it from a source that is non-human. These non-human amino acid residues often are referred to as "import" residues, which typically are taken from an "import" variable region. Humanization may be performed following the method of Winter and co-workers (see, for example, Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (see, for example, U.S. Pat. No. 4,816,567), where substantially less than an intact human variable region has been substituted by the corresponding sequence from a non-human species.

An "antibody fragment" comprises a portion of an intact antibody, such as the antigen binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody", for example, as described in U.S. Pat. No. 5,641,870 for example. Such linear antibody fragments can be monospecific or bispecific.

In certain embodiments, antibodies of the described invention are bispecific or multi-specific. Bispecific antibodies are antibodies that have binding specificities for at least two different epitopes. Exemplary bispecific antibodies can bind to two different epitopes of a single antigen. Other such antibodies can combine a first antigen binding site with a binding site for a second antigen. Alternatively, an antibody arm can be combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD16), so as to focus and localize cellular defense mechanisms to the targeted disease cell. Bispecific antibodies also can be used to localize cytotoxic agents to targeted disease cells. Bispecific antibodies can be prepared as full length antibodies or antibody fragments (for example, F(ab')2 bispecific antibodies). For example, WO 96/16673 describes a bispecific anti-ErbB2/anti-Fc gamma RIII antibody and U.S. Pat. No. 5,837,234 discloses a bispecific anti-ErbB2/anti-Fc gamma RI antibody. For example, a bispecific anti-ErbB2/Fc alpha antibody is reported in WO98/02463; U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (see, for example, Millstein et al., Nature, 305:537-539 (1983)). Similar procedures are disclosed in, for example, WO 93/08829, Traunecker et al., EMBO J., 10:3655-3659 (1991).

Alternatively, antibody variable regions with the desired binding specificities (antibody-antigen combining sites) are fused to immunoglobulin constant domain sequences. The fusion is with an Ig heavy chain constant domain, comprising at least part of the hinge, CH2, and CH3 regions. According to some embodiments, the first heavy-chain constant region (CH1) containing the site necessary for light chain bonding, is present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Techniques for generating bispecific antibodies from antibody fragments also have been described in the literature. For example, bispecific antibodies can be prepared using chemical linkage. For example, Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

Typically, the antibodies of the described invention are produced recombinantly, using vectors and methods available in the art. Human antibodies also can be generated by in vitro activated B cells (see, for example, U.S. Pat. Nos. 5,567,610 and 5,229,275). General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987, Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Human antibodies also can be produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals can be genetically engineered to produce human antibodies comprising a polypeptide of the described invention.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731;

6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

Such variant antibody sequences will share 70% or more (i.e., 80%, 85%, 90%, 95%, 97%, 98%, 99% or greater) sequence identity with the sequences recited in the application. Such sequence identity is calculated with regard to the full length of the reference sequence (i.e., the sequence recited in the application). Percentage identity, as referred to herein, is as determined using BLAST version 2.1.3 using the default parameters specified by the NCBI (the National Center for Biotechnology Information; www.ncbi.nlm.nih.gov/) [Blosum 62 matrix; gap open penalty=11 and gap extension penalty=1]. For example, peptide sequences are provided by this invention that comprise at least about 5, 10, 15, 20, 30, 40, 50, 75, 100, or more contiguous peptides of one or more of the sequences disclosed herein as well as all intermediate lengths there between. As used herein, the term "intermediate lengths" is meant to describe any length between the quoted values, such as 7, 8, 9, 10, 11, 12, 13, 14, 15, 16, 17, 18, 19, etc.; 21, 22, 23, etc.; 30, 31, 32, etc.; 50, 51, 52, 53, etc.; 100, 101, 102, 103, etc.; 150, 151, 152, 153, etc.

Compositions

This invention also provides a composition that contains a suitable carrier and one or more of the agents described above. The composition can be a pharmaceutical composition that contains a pharmaceutically acceptable carrier. The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

The above-described composition, in any of the forms described above, can be used for treating a cellular proliferative disorder. An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment.

A pharmaceutical composition of this invention can be administered to a subject parenterally, orally, nasally, rectally, topically, or buccally. The term "parenteral" as used herein refers to, but not limited to, subcutaneous, intracutaneous, intravenous, intramuscular, intraarticular, or intraarterial injection, as well as any suitable infusion technique. A sterile injectable composition can be a solution or suspension in a non-toxic parenterally acceptable diluent or solvent. Such solutions include, but are not limited to, 1,3-butanediol, mannitol, water, Ringer's solution, saline, phosphate buffer solution, and isotonic sodium chloride solution. In addition, fixed oils are conventionally employed as a solvent or suspending medium (e.g., synthetic mono- or di-glycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, TWEENS or SPANS or other similar emulsifying agents or bioavailability enhancers, which are commonly used in the manufacture of pharmaceutically acceptable solid, liquid, or other dosage forms also can be used for the purpose of formulation.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model. "Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder. An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The above-described antibodies and their antigen binding portions can be used to make antibody drug conjugates. The composition described above can contain one or more antibody drug conjugates. An "antibody-drug conjugate" or "ADC" is an antibody that is conjugated to one or more (e.g., 1 to 4) cytotoxic agents or cytotoxins, e.g., through a linker or other means. As disclosed herein, the antibody can be a monoclonal antibody specific to a cancer antigen.

The antibody drug conjugate of this invention can be used as an anticancer therapeutic for all epithelial tumors such as breast, prostate, colon, stomach, ovary, pancreas and liver cancers as well as multiple myeloma and B-cell lymphomas including Burkitt's and Diffuse Large B-cell Lymphoma. This conjugate also can be used in the treatment of some tumors such as melanoma and glioma that are not of epithelial origin due to their expression of matriptase.

Various cytotoxic agents can be used. The term cytotoxic agent refers to a substance that inhibits or prevents the function of cells and/or causes destruction of cells. Examples include chemotherapeutic agents, such as methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. The term also encompasses compounds comprising one or more radioactive isotopes (e.g., $At^{211}$, $I^{131}$, $I^{125}$ $Y^{90}$, $Re^{186}$, $Re^{188}$, $Sm^{153}$, $Bi^{212}$, and $P^{32}$).

A potent cytotoxic agent, Neocarzinostain (NCS), used clinically for hepatic artery infusion possesses potent antitumor activity. NCS is a protein-small molecule complex composed of an enediyne chromophore tightly bound to a 113 amino acid single chain protein. The chromophore is the active compound, which is responsible for DNA cleavage; while the apoprotein stabilizes and regulates the availability of the labile chromophore. The chromophore is bound non-covalently in a cleft of the binding protein and is dissociable. Upon addition of a thiol, the chromophore forms a highly reactive biradical species that can induce sequence-specific single and double strand breaks in DNA. NCS possesses antitumor activity in various human and animal tumors. As disclosed herein, the highly potent cytotoxicity of NCS toward cancer cells can be used as toxic effector component in an antibody-drug conjugate. Another example is doxorubicin" (DOX) which is an anthracycline antibiotic with a systematic (IUPAC) chemical name of (8S,10S)-10-(4-amino-5-hydroxy-6-methyl-tetrahydro-2H-pyran-2-yloxy)-6,8,11-trihydroxy-8-(2-hydroxyacety0-1-methoxy-7,8,9,10-tetrahydrotetracene-5,12-dione. Besides NCS and DOX, other examples of the agent include auristatin, calicheamicin, ricin, and tublin inhibitors.

To prepare ADCs, linker-cytotoxin conjugates can be made by convention methods analogous to those described in of Doronina et al., Bioconjugate Chem. 2006, 17, 114-124. Antibodies, typically monoclonal antibodies are raised against a specific cancer target antigen (e.g., activated matriptase), and purified and characterized. Therapeutic ADCs containing that antibody can be prepared by standard methods for cysteine conjugation, such as by methods analogous to that described in Hamblett et al., Clin. Cancer Res. 2004, 10, 7063-7070; Doronina et al., Nat. Biotechnol., 2003, 21(7), 778-784; and Francisco et al., Blood, 2003, 102, 1458-1465.

Antibody-drug conjugates with multiple (e.g., four) drugs per antibody can be prepared by partial reduction of the antibody with an excess of a reducing reagent such as DTT or TCEP at 37° C. for 30 min, then the buffer exchanged by elution through SEPHADEX G-25 resin with 1 mM DTPA in DPBS. The eluent is diluted with further DPBS, and the thiol concentration of the antibody may be measured using 5,5'-dithiobis(2-nitrobenzoic acid) [Ellman's reagent]. An excess, for example 5-fold, of the linker-cytotoxin conjugate is added at 4° C. for 1 hr, and the conjugation reaction may be quenched by addition of a substantial excess, for example 20-fold, of cysteine. The resulting ADC mixture may be purified on SEPHADEX G-25 equilibrated in PBS to remove unreacted linker-cytotoxin conjugate, desalted if desired, and purified by size-exclusion chromatography. The resulting ADC may then be then sterile filtered, for example, through a 0.2 μm filter, and lyophilized if desired for storage.

The ADCs of this invention may be assayed for binding affinity to and specificity for the desired antigen by any of the methods conventionally used for the assay of antibodies; and they may be assayed for efficacy as anticancer agents by any of the methods conventionally used for the assay of cytostatic/cytotoxic agents, such as assays for potency against cell cultures, xenograft assays, and the like as described in the examples below. A person of ordinary skill in the art will have no difficulty in determining suitable assay techniques; from the results of those assays, in determining suitable doses to test in humans as anticancer agents, and, from the results of those tests, in determining suitable doses to use to treat cancers in humans.

An ADC of this invention, like the antibody of this invention, can be formulated as solutions for intravenous administration, or as lyophilized concentrates for reconstitution to prepare intravenous solutions (to be reconstituted, e.g., with normal saline, 5% dextrose, or similar isotonic solutions). They can be administered by intravenous injection or infusion. A person of ordinary skill in the art will have no difficulty in developing suitable formulations.

EXAMPLE 1

This example demonstrates the cytoxic potency of NCS conjugated to the monoclonal antibody (M69) targeted to activated matriptase in tumor cells To demonstrate the cytotoxic potency of NCS conjugated to M69 for tumor-specific delivery, a prototype conjugate, M69-NCS, was generated by using the SMCC-based linker as described in the method of M69-DOX synthesis. More specifically, monoclonal antibodies against matriptase M69 (Lin C. Y., et al., J. Biol. Chem., 1999, 274 (26): 18237-18242; Chen, Y. W., et al. J. Biol. Chem., 2010, 285 (41):31755-31762) was conjugated to DOX (SIGMA) using Protein-Protein Coupling kit (INVITROGEN) according to the manufacture's instruction with some minor modification. Briefly, NCS was reacted with crosslinker SMCC (succinimidyl-4-(N-maleimidomethyl)cyclohexane-1-carboxylate) at a molar ratio (MR) between 1:3 and 1:1.5 (NCS: SMCC) for 1 hour at room temperature with constant stirring. About 200 mg M69 mAb was reacted with SPDP (Succinimidyl 3-(2-pyridyldithio)-propionate) for 1 hour at room temperature followed by exchange of phosphate buffer using Centrifugal Filter Device (ULTRAFREE, MILLIPORE). Alternatively, the mAb can be separated from free SPDP by gel filtration with SEPHADEX G50. NCS maleimide derivative was then conjugated to thiolated M69 mAb for 3 hours at room temperature followed by DEAE column with salt concentration gradient from 0-0.3 M NaCl in 10 mM Tris buffer (pH 7.4) to separate the free NCS and the antibody conjugate.

The in vitro cytotoxic efficacy of M69-NCS toward various cancer cells was assessed and the IC50 values of M69-NCS were summarized in the Table 1 for comparison. Bone marrow-derived mesenchymal cells that lack expression of matriptase, and immortalized human mammary epithelial cells, AlN4, in which a very low level of activated matriptase, found only at cell-cell junctions, were used as controls to test cytotoxic activity. Breast cancer cells, MDA-MB 468, were sensitive to the NCS conjugate with an IC50 of 25 ng/ml (Table 1).

Moreover, both pancreas (PNAC1) and liver cancer (HepG2) cells were also sensitive to the conjugate at these low concentrations (Table 1). The NCS conjugate showed less cytotoxic potency toward prostate cancer cell line, DU145, which expressed less activated matriptase on the cell surface. While DU145 cells were less vulnerable to the conjugate, the IC50 values were decreased from 1.5 to 0.7 mg/ml under hypoxic conditions (Table 1).

Cells expressing much lower levels of activated matriptase, like immortalized mammary epithelial cells, A1N4, were less sensitive to the NCS conjugate compared to the breast cancer cell line, MDA-MB468, demonstrating that the cytotoxic activity of the conjugate is mediated through the antigen expression on the cell surface. Moreover, normal cells such as bone marrow-derived mesenchymal stromal cells that lack expression of matriptase are even more resistant to M69-NCS (IC50=4 µg/ml, see Table 1). The difference in the IC50s of M69-NCS between antigen-positive tumor cells (MDA-MB 468) vs antigen-negative normal stromal cells is 160 fold.

TABLE 1

IC50 values of M69-NCS toward various tumor cells.
Cell proliferation assay with colorimetric method (MTS assay; Promega) was used to assess cytotoxic effects of M69-NCS conjugate on various types tumor was used to assess cytotoxic effects of M69-NCS conjugate on various types tumor cells as indicated and normal bone marrow-derive mesenchymal stromal cells as well as immortalized mammary epithelial cells. The obtained IC50 values were listed on the table above. For DU145 cells under hypoxic condition, the IC50 was also evaluated.

| Cancer | Cell line | IC50 |
|---|---|---|
| Breast | MDA-MB 468 | 25 ng/ml |
| Pancreas | PANC1 | 40 ng/ml |
| Liver | HepG2 | 60 ng/ml |
| Prostate | DU145 | 1.5 µg/ml; 0.7 µg/ml (hypoxia) |
| Immortalized epithelial cells | A1N4 | 400 ng/ml |
| Normal cells | Bone marrow-derived stromal cells | 4 □□ µg/ml |

EXAMPLE 2

This example describes the cloning and sequencing the gene encoding the variable regions and generating a humanized version of M17, another monoclonal antibody specifically targeting activated matriptase.

Total RNA was extracted from $10^7$ hybridoma cells (M17) that secreted monoclonal antibody against activated matriptase by using total RNA extraction with TRIZOL Reagent and Purification System (INVITROGEN). About 0.5 µg of RNA was reverse transcribed by Oligo dT-Adaptor primers of the first-strand cDNA synthesis kit (SUPERSCRIPT III Cells Direct cDNA synthesis system, INVITROGEN). cDNA encoding the mouse variable heavy ($V_H$) and light ($V_L$) chains were amplified by RT-PCR with degenerated immunoglobulin PCR primers (35 cycles at 94° C. for 30 sec, 55° C. for 30 sec and 72° C. for 1 min). The primers for amplification of variable regions of the immunoglobin gene family were based on the design of Rohatgi et al. J Immunol Methods. 2008 Dec. 31; 339(2):205-19. The DNA fragments encoding variable region of VH and light $V_L$ chains were amplified by PCR with following primers ($V_H$: forward primer, CAGTGTGAGGTGAAGCTGGT (SEQ ID NO: 5) and reverse primer, GCACCTCCAGATGTTAACT (SEQ ID NO: 6); $V_L$: forward primers, CTGCTGCTCTGGGTTCC (SEQ ID NO: 7) and reverse primer, GCACCTCCAGATGTTAACTG (SEQ ID NO: 8)). The PCR generated DNA fragments encoding $V_H$ and $V_L$ were cloned into TOPO® cloning vector (INVITROGEN) for nucleotide sequencing. The obtained DNA sequences and deduced amino acid sequences are shown below.

```
        E   V   K   L   V   E   S   G   G   G   L   V   Q   P   G   G   S   R   K   L
    1   GAAGTGAAGCTGGTGGAGTCTGGGGGAGGCTTAGTGCAGCCTGGAGGGTCCCGGAAACTC

S   C   A   A   S   G   F   T   F   S   S   F   G   M   H   W   V   R   Q   A
   61   TCCTGTGCAGCCTCTGGATTCACTTTCAGTAGCTTTGGAATGCACTGGGTTCGTCAGGCT

P   E   K   G   L   E   W   V   A   Y   I   S   S   G   S   S   T   L   H   Y
  121   CCAGAGAAGGGGCTGGAGTGGGTCGCATACATTAGTAGTGGCAGTAGTACCCTCCACTAT

A   D   T   V   K   G   R   F   T   I   S   R   D   N   P   E   N   T   L   F
  181   GCAGACACAGTGAAGGGCCGATTCACCATCTCCAGAGACAATCCCGAGAACACCCTGTTC

L   L   M   K   L   P   S   L   C   Y   G   L   L   G   S   R   N   L   S   P
  241   CTGCTAATGAAACTACCCTCACTATGCTATGGACTACTGGGGTCAAGGAACCTCAGTCCC

R   V   L   Q   (SEQ ID NO: 1)
  301   CGTGTCCTCCAG (SEQ ID NO: 3)

M17 VL
        L   L   L   W   I   P   G   S   T   G   D   I   V   L   T   Q   S   P   A   S
    1   CTGCTGCTCTGGATTCCAGGTTCCACAGGTGACATTGTGCTGACCCAATCTCCAGCTTCT

L   A   V   S   L   G   Q   R   A   T   I   S   C   R   A   S   E   S   V   D
   61   TTGGCTGTGTCTCTAGGGCAGAGGGCCACCATCTCCTGCAGAGCCAGCGAAAGTGTTGAT

N   Y   G   I   S   F   M   N   W   F   Q   Q   K   P   G   Q   P   P   K   L
  121   AATTATGGCATTAGTTTTATGAACTGGTTCCAACAGAAACCAGGACAGCCACCCAAACTC

L   I   Y   A   A   S   N   Q   G   S   G   V   P   A   R   F   S   G   S   G
  181   CTCATCTATGCTGCATCCAACCAAGGATCCGGGGTCCCTGCCAGGTTTAGTGGCAGTGGG

S   G   T   D   F   S   L   N   I   H   P   M   G   E   A   D   T   A   M   Y
  241   TCTGGGACAGACTTCAGCCTCAACATCCATCCTATGGGGGAGGCAGATACTGCAATGTAT
```

```
                  F   C   Q   Q   S   K   E   V   P   Y   T   F   G   G   G   T   K   L   E   I
301   TTCTGTCAGCAAAGTAAGGAGGTCCCGTACACGTTCGGAGGGGGGACCAAGCTGGAAATA

K   R   A   D   A   A   P   T   V   S   I   F   P   P   S   S   E   Q   L   T
361   AAACGGGCTGATGCTGCACCAACTGTATCCATCTTCCCACCATCCAGTGAGCAGTTAACA

S   G   G   (SEQ ID NO: 2)
421   TCTGGAGGT (SEQ ID NO: 4)
```

EXAMPLE 3

This example describes the generation and assessment of a conjugate using M17 to determine its in vitro cytotoxic efficacy toward breast cancer cells in the same manner described above in Example 1.

In order to demonstrate that M17 may be used for targeted delivery of cytotoxic agents, a conjugate was generated by coupling the mAb with DOX via thioether bond formed by the SMCC reaction (Protein-Protein Crosslinking Kit, INVITROGEN). To assess the cytotoxic effect of M17-DOX toward breast cancer cells MDA-MB468, the MTS cell proliferation assay was performed. Similar to M69-DOX, the DOX conjugate coupled to M17 mAb killed cancer cells in a dose-dependent manner (FIG. 1). A much lower IC50 value of the M17 conjugate at 0.65 µg/ml indicates that M17-DOX is much more potent than M69-DOX, where the IC50 is 10 µg/ml). This DOX conjugate demonstrates that M17, like M69 is capable of effective delivery of toxic molecules to tumor cells.

The effects of this conjugate on xenografts of the MDA-MB468 in nude mice are also tested. It is expected that it inhibits tumor growth in nude mice.

EXAMPLE 4

This example describes the generation of an M17-NCZ conjugate by generating the recombinant chimeric M17 mAb and adding chromophore.

The M17 mAb is conjugated to potent toxic agents such as neocarzinostatin. In addition, other highly toxic agents such as derivatives of auristatin and maytansinoid are also utilized to construct new ADCs targeting activated matriptase by using optimal linker technologies. The recombinant chimeric mAb can bind with the chromophore with defined stoichiometry that depends on the number of apo-NCS in the protein construct.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. An isolated antibody, or antigen binding portion thereof, comprising a heavy chain and a light chain that comprise the sequences of SEQ ID NOs: 1 and 2, respectively, wherein the antibody specifically recognizes the active form of matriptase and wherein the antibody or binding portion is conjugated with a cytotoxic agent.

2. The isolated antibody of claim 1, or antigen binding portion thereof, wherein the antibody is a single-chain antibody, a monoclonal antibody, a humanized monoclonal antibody, or a human monoclonal antibody.

3. The isolated antibody of claim 1, or antigen binding portion thereof, wherein the cytotoxic agent is doxorubicin, auristatin, maytansinoid, neocarzinostatin (NCS), or a derivative thereof.

4. The isolated antibody of claim 3, or antigen binding portion thereof, wherein the cytotoxic agent is NCS or a derivative thereof.

5. An isolated antibody, or antigen binding portion thereof, comprising a heavy chain and a light chain that comprise the sequences of SEQ ID NOs: 1 and 2, respectively, wherein the antibody specifically recognizes the active form of matriptase.

6. An isolated polypeptide comprising the sequence of SEQ ID NO: 1 or 2.

7. A pharmaceutical composition comprising (i) at least one antibody of claim 1, or antigen binding portion thereof, and (ii) a pharmaceutically acceptable carrier.

8. A method of treating a cellular proliferative disorder, comprising the steps of:
   (a) identifying a subject in need of such prevention or treatment, and
   (b) administering to said subject a first therapeutic agent comprising a therapeutically effective amount of at least one antibody of claim 1, or antigen binding portion thereof.

9. The method of claim 8, further comprising administering to the subject a second therapeutic agent.

10. The method of claim 8, wherein the cellular proliferative disorder is cancer.

11. The method of claim 10, wherein the cellular proliferative disorder is one selected from the group consisting of breast cancer, lung cancer, prostate cancer, colon cancer, stomach cancer, ovary cancer, pancreas cancer, liver cancer, mesotheleoma, melanoma, glioma, myeloma, and lymphoma.

* * * * *